United States Patent [19]
Riesgo et al.

[11] Patent Number: 5,935,857
[45] Date of Patent: Aug. 10, 1999

[54] BLOOD DILUENT

[75] Inventors: Mirta I. Riesgo; Carole Jo Young, both of Miami, Fla.

[73] Assignee: Coulter International Corp., Miami, Fla.

[21] Appl. No.: 08/904,477

[22] Filed: Aug. 1, 1997

[51] Int. Cl.⁶ .................................................. G01N 31/00
[52] U.S. Cl. ................................ 436/18; 436/8; 436/10; 436/17; 436/63; 435/2; 252/408.1
[58] Field of Search .................................. 436/8, 10, 18, 436/17, 63, 164, 166, 174, 176; 435/2, 29, 30, 39; 252/408.1

[56] References Cited

U.S. PATENT DOCUMENTS

| | | | |
|---|---|---|---|
| 3,962,125 | 6/1976 | Armstrong | 436/18 |
| 4,185,964 | 1/1980 | Lancaster | 436/17 |
| 4,213,876 | 7/1980 | Crews et al. | 436/18 |
| 4,255,385 | 3/1981 | Stroupe et al. | 422/61 |
| 4,322,313 | 3/1982 | Raaijmakers | 436/2 |
| 4,346,018 | 8/1982 | Carter et al. | 436/17 |
| 4,485,175 | 11/1984 | Ledis et al. | 436/63 |
| 4,506,018 | 3/1985 | North, Jr. | 436/10 |
| 4,521,518 | 6/1985 | Carter et al. | 436/10 |
| 4,528,274 | 7/1985 | Carter et al. | 436/10 |
| 4,529,705 | 7/1985 | Larsen | 436/17 |
| 4,617,275 | 10/1986 | Matsuda et al. | 436/10 |
| 4,656,139 | 4/1987 | Matsuda et al. | 436/17 |
| 4,745,071 | 5/1988 | Lapicola et al. | 436/63 |
| 4,962,038 | 10/1990 | Carter et al. | 436/10 |
| 4,968,629 | 11/1990 | Lapicola | 436/18 |
| 5,008,202 | 4/1991 | Edmondson et al. | 436/18 |
| 5,227,304 | 7/1993 | Wong | 436/17 |
| 5,242,832 | 9/1993 | Sakata | 436/17 |
| 5,250,438 | 10/1993 | Ryan | 436/17 |
| 5,691,204 | 11/1997 | Kim et al. | 436/63 |
| 5,733,784 | 3/1998 | Studholme et al. | 436/63 |

FOREIGN PATENT DOCUMENTS

WO 95/24651  9/1995  WIPO .

*Primary Examiner*—Maureen M. Wallenhorst
*Attorney, Agent, or Firm*—Mitchell E. Alter

[57] ABSTRACT

An improved isotonic multipurpose blood diluent, and a method for use of this diluent is provided. The diluent is especially suitable for electronic enumeration and sizing of blood cells, determination of hemoglobin parameters and differentiation of leukocyte subpopulations in a single blood cell sample using a cyanide free lytic reagent. The diluent finds particular applicability over wide operating temperatures.

19 Claims, No Drawings

BLOOD DILUENT

BACKGROUND OF THE INVENTION

1. Technical Field of the Invention

This invention relates to the fields of hematology and immunology and to improvements in reagents used for analyzing blood cells. More specifically, the present invention relates to an improved diluent especially suited for enumeration and sizing of blood cells, determination of hemoglobin parameters and differentiation of leukocyte subpopulations in a single blood cell sample by means of suitable electronic instrumentation.

2. Discussion of the Prior Art

It is a common medical diagnostic procedure to analyze a blood sample of a patient in order to make certain classic determinations with respect to the blood sample. This procedure is an important tool for the physician. Important parameters are referred to as red blood cell count (RBC), hematocrit (HCT), hemoglobin (HGB), mean corpuscular volume (MCV), mean corpuscular hemoglobin (MCH), mean corpuscular hemoglobin concentration (MCHC), platelet count (PLT) and mean platelet volume (MPV). These parameters are included in a complete blood count (CBC). Other important determinations are white blood cell count (WBC) and differentiation of the white blood cells into three or more subpopulations.

In general, blood cell analysis comprises diluting a blood sample with a fluid which functions as a diluent, analyzing one portion of the diluted blood sample for red blood cell and platelet parameters and contacting the other portion of the diluted blood sample with a lytic reagent to remove the erythrocytes and platelets to enable enumeration and differentiation of leukocytes. One of the earliest diluents reported was physiological saline. More advanced diluents for whole blood samples typically contained certain physiological salts, specific buffers, and preservative agents. In addition, the use of other reagents in blood cell analysis, including anticoagulants in the blood sample, detergents, monoclonal antibodies, dyes and stains results in unpredictable interactions among the biological sample and the chemical reagents, especially over varying operating temperatures.

Because of the sensitivity of erythrocytes, leukocytes, platelets and hemoglobin concentration to the chemical reagents, it has been very difficult to find a combination of chemical reagents that do not degrade or undesirably alter the characteristics of the cells to be analyzed and hemoglobin parameters, especially over varied operating temperature conditions. Frequently, a component is added, for example a preservative to maintain the stability of a reagent, but which might seriously and detrimentally affect physical parameters of the cells. Or a component is added to a diluent for a certain functional property, but that component will adversely affect other blood cell determinations. In one such example, the addition of a component to stabilize leukocytes has been found to adversely affect hemoglobin concentration determinations.

Because the cell's physical parameters are affected by the constituents of any diluent and by the method of analysis, whether automated, semiautomated or manual, prior art diluents have been formulated specifically for use with a specific test or specific instrument. These prior art diluents have not been universal or multipurpose in the sense that they could be used in various test instruments or with various test methods. For example, generally, a commercial diluent used for hematology analysis is different from one used for fluorescence flow cytometer analysis because of the problems of diluent fluorescence or compatibility of the diluent to fluorescence probes or monoclonal antibodies.

Many of the prior art diluents have one or more shortcomings depending upon the instrument, operating temperature, age of the sample, and the specific parameters of the sample which are to be determined. Blood diluents for use in automatic hematology instruments have been described in U.S. Pat. Nos. 3,962,125 to Armstrong; 4,185,964 to Lancaster; 4,213,876 to Crews et al.; 4,529,705 to Larsen; 4,617,275 to Matsuda et al.; 4,745,071 to Lapicola et al.; 4,485,175 to Ledis et al.; 4,346,018; 4,521,518 and 4,962,038 to Carter et al.; 4,968,629 to Lapicola; and 5,250,438 to Ryan. In addition, the following patents provide additional information concerning blood diluents and their use.

U.S. Pat. No. 4,255,385 to Stroupe et al. describes a method and reagent for determining hemoglobin in blood samples. The reference discloses a reagent for lysing and diluting a whole blood sample for cell analysis. The reagent contains potassium ferricyanide for the hemoglobin determination.

U.S. Pat. No. 4,506,018 to North describes a blood diluent for avoiding blood cell volume changes by balancing the effects of a preservative and a surfactant used in the diluent.

U.S. Pat. No. 4,656,139 to Matsuda et al. describes a method of preparing cells for blood analysis comprising the steps of diluting a blood sample with a diluent comprising boric acid buffer solution, ethylenediaminetetraacetic acid (EDTA) and (2-pyridylthio-1-oxide) sodium. The (2-pyridylthio-1-oxide) sodium is employed to enable a hemoglobin determination.

U.S. Pat. No. 5,008,202 to Edmondson et al. describes a blood diluent and method for diluting blood for use in blood cell analysis. The blood diluent generally comprises an organic buffer, a cell stabilizing agent, an inorganic salt, a solvent and EDTA, wherein EDTA serves as an antimicrobial agent, or a mixture of EDTA and sodium fluoride wherein together they serve as an antimicrobial agent.

U.S. Pat. No. 5,227,304 to Wong describes a complicated reagent system for enumeration and sizing of blood cells in a Cell Dyn® brand blood analyzer. The reagent system comprises an isotonic diluent and detergent, wherein the diluent comprises an imidazole organic buffer, antimicrobial agent, inorganic salts and pH adjusting agent. In the specification, Wong teaches EDTA as a chelator and to enhance the antimicrobial character of the diluent, wherein the antimicrobial agents are sodium omadine [2-pyridinethiol-1-oxide] and Triadene 3 [hexahydro-1,3,5-tris(2-hydroxyethyl)-s-triazine] or Triadene 10 [a mixture of 60% Triadene 3 and 6% sodium omadine]. (Sodium Omadine is a registered trademark of the Olin Corporation.)

U.S. Pat. No. 5,242,832 to Sakata describes a lytic reagent containing imidazole and imidazole derivatives as a hemoglobin stabilizer.

PCT Patent Application WO 95/24651 to Kim et al. describes a lytic reagent for use in total hemoglobin measurements containing lauryl dimethylamine oxide as a lytic agent and imidazole and its derivatives as a hemoglobin stabilizer. The lytic reagent is used to lyse erythrocytes for hemoglobin determinations without using cyanide. However, this reagent system is not used for any other blood cell analysis such as WBC or leukocyte differentiation.

Notwithstanding the prior art diluents, there still exists a need for a multipurpose diluent which minimizes the need for several diluents and which can be used in a varied temperature environment. A multipurpose diluent avoids the costs, inconvenience and potential confusion caused by stocking a variety of different diluents within a given clinical laboratory to accommodate the requirements of a specific hematology analyzer or flow cytometer analyzer and specific analysis performed on each such analyzer.

SUMMARY OF THE INVENTION

In view of the foregoing, an object of the invention is to provide an improved diluent and method of using an improved diluent to determine red blood cell parameters, including hemoglobin concentration, and platelets in a blood sample. A further object of the invention is to provide an improved diluent and method of using the improved diluent to determine white blood cell count and leukocyte subpopulations in a blood sample.

Accordingly, the present invention provides a multipurpose blood diluent not containing hexahydro-1,3,5 tris(2-hydroxethyl)-s-triazine useful in analysis of red blood cells, white blood cells, platelets and hemoglobin concentration in a blood sample. The diluent comprises a first compound selected from ethylenediamine tetraacetic acid, ethylenediamine tetraacetic acid derivatives and combinations thereof; a second compound selected from imidazole, imidazole derivatives and combinations thereof; an alkaline metal chloride; a third compound selected from alkaline metal sulfate and alkaline metal salts of organic acids selected from tartrate, formate, lactate, acetate, citrate and pyruvate and combinations thereof, wherein the first compound and second compound are in an amount effective to provide reproducible hemoglobin and cell volume measurements over a temperature range from 55° F. to 105° F. and wherein said diluent is an electrolyte capable of conducting electrical current, isotonic so that it stabilizes blood cell volume and has a neutral pH.

The invention further provides a method for analyzing a blood sample containing blood cells comprising a) mixing a blood sample containing blood cells with a multipurpose blood diluent, said diluent comprising i) a first compound selected from ethylenediamine tetraacetic acid, ethylenediamine tetraacetic acid derivatives and combinations thereof; ii) a second compound selected from imidazole, imidazole derivatives and combinations thereof; iii) an alkaline metal chloride; iv) a third compound selected from alkaline metal sulfate and alkaline metal salts of organic acids selected from tartrate, formate, lactate, acetate, citrate and pyruvate and combinations thereof; wherein said diluent does not contain hexahydro-1,3,5 tris(2-hydroxethyl)-s-triazine; and wherein the first compound and second compound are in an amount effective to provide reproducible hemoglobin and cell volume measurements over a temperature range from 55° F. to 105° F. and wherein said diluent is an electrolyte capable of conducting electrical current, isotonic so that it stabilizes blood cell volume and has a neutral pH; and b) analyzing said diluted blood sample to determine at least one physical parameter of said blood cells.

DETAILED DESCRIPTION OF THE PREFERRED EMBODIMENTS

The multipurpose diluent of the present invention is useful in analysis of a blood sample. In a first embodiment, the diluent is useful for the determination of red blood cell, hemoglobin and platelet measurements. Measurements include cell size, shape, content and volume. Measurements can be made using light scatter, low frequency current, radio frequency current, fluorescence and combinations thereof. In a second embodiment, the diluent is useful for the determination of WBC and differentiation of leukocytes into three subpopulations. In a third embodiment, the diluent is useful as a sheath fluid in focused flow cytometry for determination of five subpopulations of leukocytes. In a fourth embodiment, the diluent is useful for fluorescence flow cytometry analysis when using fluorescence probes or antibodies.

The diluent is shelf stable and can be used over a wide range of operating temperatures. In addition, it can be used with fresh or aged blood samples. Measurements obtained from using the diluent of this invention are comparable to measurements obtained from using a commercially available diluent.

The diluent contains a first compound selected from ethylenediamine tetraacetic acid (EDTA), EDTA derivatives and combinations thereof. The EDTA derivatives include salts of EDTA, such as disodium EDTA, and ethyleneglycol-bis-(3-aminoethylether) N-N'-tetraacetic acid (EGTA). The preferred first compound is disodium EDTA. The range of the first compound is from 2.5 grams per liter (g/L) to 11 g/L. The preferred amount of the first compound is from 3 to 8 g/L.

The diluent also contains a second compound selected from imidazole, imidazole derivatives and combinations thereof. The imidazole derivatives include phenylimidazole, methylimidazole, ethylimidazole and butylimidazole. The range of the second compound is from 0.5 g/L to 9 g/L. The preferred amount of the second compound is from 2 to 4 g/L. It has been found that the second compound is a compatible pH buffer in the multipurpose diluent.

While not desiring to be bound by any theory of the invention, it is presently believed that the combination of the first compound and second compound affects individual blood cells so that when a blood sample is analyzed for one or more measurements, the blood sample consistently provides the same measurement over a temperature range from 55° F. to 105° F., preferably 60° F. to 90° F. This performance stability over a wide temperature range is an important feature of the present invention because temperature variations from a instrument standard operating temperature can cause variations in measurements.

The diluent further contains an alkaline metal chloride. Suitable alkaline metal chlorides include the metals selected from the group consisting of sodium and potassium. The range of the alkaline metal chloride is from 0.1 to 5.0 gm/L. The preferred amount of the alkaline metal chloride is from 0.5 to 3.5 gm/L.

The diluent also contains a third compound selected from i) alkaline metal sulfate and ii) alkaline metal salts of organic acids selected from tartrate, formate, lactate, acetate, citrate and pyruvate and combinations thereof. Suitable alkaline metal sulfates include the metals selected from the group consisting of sodium and potassium. The range of the third compound is from 8 to 35 gm/L. The preferred amount of the third compound is from 10 to 25 gm/L. The preferred third compound is an alkaline metal sulfate. The most preferred third compound is sodium sulfate.

The alkaline metal chloride and alkaline metal sulfate are used to provide a suitable osmolality so as not to adversely affect cell volume. Generally, the multipurpose diluent will be iso-osmotic. More specifically, the osmolality will be about 200 to 400 milliosmoles (mOsm), and preferably from 250 to 380 mOsm and most preferably from 290 to 350 mOsm. However, the osmolality of the multipurpose diluent can vary when used with a lytic reagent composition. The volume of the multipurpose diluent can be adjusted relative to a lytic reagent volume so that the final osmolality of the blood sample mixture is between approximately 290 to 350 mOsm, preferably from 310 to 330 mOsm. In addition, when used as a sheath fluid in a flow instrument, the relationship between the osmolality and conductivity of the sheath fluid and the osmolality and conductivity of the core fluid should be maintained. For example, the diluent will typically have a conductivity from about 15 to 23 mS/cm.

The pH of the multipurpose diluent is selected for the instrument and test to be used. Generally, the diluent will have a pH from about 6 to about 7.8. For automated and semiautomated instruments which perform volume distribution counting, the pH ranges from pH 6.5 to pH 7.6, preferably pH 6.6 to 7.4. For flow cytometry instruments, when used as a sheath fluid, the pH ranges from about pH 7.0 to about 7.2.

To obtain a pH value for the diluent in the above pH range, a pH adjusting agent can be used. Examples of pH adjusting agents which are suitable to impart the required pH include acids, typically hydrochloric or sulfuric, and bases, such as alkali metal hydroxides. Other acids may be substituted provided that they do not interfere with the analysis of the blood sample. Examples of acceptable alkali metal hydroxides include sodium hydroxide and potassium hydroxide.

The reagent composition should have such other characteristics to make it compatible with its intended use. First, the compounds used in the multipurpose diluent should not degrade during the shelf life of the product. The shelf life of the product takes into account the time from manufacture of the product through the time of customer usage of the product. During this time, the chemical functionality of the product needs to be maintained. Preferably, the diluent has a shelf life greater than 12 months. It has been found that the combination of compounds in the present formulation meets this requirement.

Second, the multipurpose diluent will also contain a preservative composition to avoid fungal or bacterial growth which might adversely affect the physical characteristics or functionality of the diluent. Preferably, the multipurpose diluent will not contain sodium 2-pyridinethiol-1-oxide (sodium omadine), hexahydro-1,3,5 tris(2-hydroxyethyl)-s-triazine (Triadine-3), 1-hydroxypryridine-2-thione, sodium salt of 2 pyridythiol-1 -oxide, 1,3-dimethylurea, 1,3-dimethylolurea or sodium fluoride. It has been found that the sodium omadine is unstable to light and oxidizing agents which can adversely affect product functionality. Similarly, 1,3 dimethylurea and 1,3-dimethylolurea do not provide reproducible determination of hemoglobin concentration because it adversely reacts with the hemoglobin changing the spectrophotometric characteristics. The use of sodium fluoride is not a suitable preservative since it has been found to react with glass cuvettes.

The quantity of the preservative should not adversely affect the analysis of the whole blood sample. The quantity of the preservative composition can be determined by routine experimentation by one skilled in the art, and is typically less than 0.5% by weight of the diluent.

Suitable preservatives include 1) organic and inorganic acids: such as, sorbic acid, benzoic acid, salicylic acid, dehydroacetic acid; 2) esters and salts: such as, esters of p-hydroxybenzoic acid (parabens); 3)substituted aliphatic diol derivatives of 1,3-dioxane: such as, 6-Acetoxy-2,4-dimethyl-1,3-dioxane, 5-Bromo-5-nitro-1,3-dioxane; 4) derivatives of imidazole: such as, 1,3-di(hydroxymethyl)-5-5-dimethyl-2,4-dioxoimidazole, N-N"-methylene bis [5'-[1-hydroxymethyl]-2,5-dioxo4-imidazolidinyl urea], mono and dimethylol dimethyl hydantoin; 5) isothiazolones: such as, 5-chloro-2-methyl4-isothiazolin-3-one, 2-methyl4-isothiazolin-3-one, 1,2-benzisothiazolin-3-one; and sodium hydroxymethylglycinate; and cis-1 -(3-chloroallyl)-3,5,7-triaza-1-azoniaadamantane chloride. The preferred preservatives are n-(hydroxymethyl)-N-(1,3-dihydroxymethyl-2,5-dioxo4-imidazolidinyl)-N'-(hydroxymethyl)urea and 5-chloro-2-methyl4-isothiazolin-3-one with 2-methyl-4-isothiazolin-3-one.

Optionally, the diluent can include an anesthetic which acts as a cell stabilizing agent. The cell stabilizer is used to stabilize cell size, shape and integrity of blood cellular components: such as preventing platelet aggregation. The precise quantities of the cell stabilizing agent used may vary as dictated by their chemical formulation. Typically, the cell stabilizing agent is less than 0.5% by weight of the diluent. Suitable cell stabilizing agents include 4-aminobenzoic acid esters and derivatives thereof having the structures $RHN-C_6H_4-COOR'$ or $RHN-C_6H_4-COOCH_2CH_2R'$ where R is hydrogen and lower alkyl, and R' is lower alkyl, dialkylaminoalkyl and dialkylamino. Examples of such compounds include benzocaine, procaine, butacaine, tetracaine and butethamine. These compounds are useful as a base or as a salt thereof, for example the hydrochloride, butyrate, nitrate or borate. Some specific examples of cell stabilizing agents which have been found to be compatible with the other diluent components comprise dimethylolurea, 4-aminobenzoic acid-2-(diethylamino)ethyl ester hydrochloride and 2-(diethylamino)-N-(2,6-dimethylphenyl) acetamide. The preferred cell stabilizing agent is 4-(butylamino)benzoic acid-2-(dimethylamino)ethyl ester hydrochloride.

A multipurpose diluent composition according to this invention is illustrated in Table 1, below:

TABLE 1

DILUENT COMPOSITION

| Component | Range (grams/liter) | Preferred (grams/liter) |
|---|---|---|
| First Compound | 2.5 to 11 | 3 to 8 |
| Second Compound | 0.5 to 9 | 2 to 4 |
| Alkaline metal chloride | 0.1 to 5 | 0.5 to 3.5 |
| Alkaline metal sulfate | 8 to 35 | 10 to 25 |
| Antimicrobial | Effective amount | 0.1 to 3 |
| Acid or Base | Sufficient to obtain pH 6.5–7.6 | 6.6 to 7.4 |
| Water | Fill to 1 liter | |

EXAMPLE 1

Three multipurpose diluents were prepared using the components and preferred ranges listed in Table 1, varying the EDTA concentration at 0, 3 and 7.5 g/L respectively. A commercial hematology control, a commercial hematology calibrator and three fresh bloods were tested on a COULTER COUNTER® S Plus IV diff hematology analyzer. The instrument was placed in an environmental chamber with a controlled temperature at 60° F. Table 2 indicates the relationship in cell volume and EDTA concentration demonstrating that EDTA concentration affects cell volume at 60° F.

TABLE 2

EFFECT OF EDTA ON THE MCV FOR CALIBRATOR, BLOOD CELL CONTROL AND FRESH BLOODS AT 60° F.

| EDTA concentration (g/L) | 0.0 | 3.0 | 7.5 |
|---|---|---|---|
| Calibrator | 89.4 | 88.5 | 88.7 |
| Blood Cell Control | 88.0 | 88.0 | 87.5 |
| Fresh Blood #1 | 76.3 | 76.0 | 75.0 |
| Fresh Blood #2 | 85.3 | 84.3 | 83.8 |
| Fresh Blood #3 | 90.6 | 90.0 | 89.4 |

EXAMPLE 2

Certain red blood cell parameters, such as MCV, change at temperatures below 75° F. A commercial diluent control in Table 3A was compared to the diluent of this invention in Table 3B. The test samples were tested on a COULTER COUNTER S Plus IV diff hematology analyzer. The diluent of this invention renders the blood cell volume of the control, calibrator and fresh bloods less sensitive to changes at 60° F.

TABLE 3A

Diluent Control - MCV

|  | 60° F. | 75° F. | 75–60° F. |
|---|---|---|---|
| Calibrator | 86.0 | 86.1 | 0.1 |
| Blood cell control | 95.5 | 94.1 | −1.4 |
| Fresh Blood #1 | 79.7 | 81.3 | 1.6 |
| Fresh Blood #2 | 86.6 | 88.5 | 1.9 |

TABLE 3B

Diluent of the Invention - MCV

|  | 60° F. | 75° F. | 75–60° F. |
|---|---|---|---|
| Calibrator | 87.5 | 86.6 | −0.9 |
| Blood cell control | 96 | 95.8 | −0.2 |
| Fresh Blood #1 | 80.2 | 80.5 | 0.3 |
| Fresh Blood #2 | 86.8 | 87.6 | 0.8 |

EXAMPLE 3

The diluent of Table 1 is especially suitable for use with a blood sample which is passed through a hematology analyzer of the type manufactured by Coulter Corporation, Miami, Fla. The blood sample is analyzed to obtain certain physical parameters of red blood cells and volume differentiation of the leukocytes into at least three subpopulations of lymphocytes, monocytes and granuloctyes. In using the multipurpose diluent of Table 1, a cyanide free lytic reagent was used which comprised a mixture of:

|  | Amount (grams/liter) |
|---|---|
| dodecyl trimethyl ammonium chloride and tetradecyl trimethyl ammonium bromide | 32 |
| antioxidant | 2 |
| Disodium EDTA | 2.5 |
| Pluronic 25R8 Prill | 1 |

The WBC, RBC and platelet parameters, including the differentiation of the white blood cells into three subpopulations, using this reagent system are consistent over a temperature range from 60 to 85° F.

EXAMPLE 4

A multipurpose diluent was prepared using the components and preferred ranges listed in Table 1. Fresh bloods from normal donors and clinical abnormal samples were tested on a COULTER® STKS hematology analyzer. The instrument was placed in an environmental chamber at a controlled temperature 60° F. and a portion of the fresh blood samples were tested. Thereafter, the temperature was raised to 85° F. and another portion of the fresh blood samples were tested. In addition, for each test conducted at extreme temperatures, a comparator instrument was run at 75° F., using another portion of the fresh blood samples. The following Table 4 presents mean values for recovered hemoglobin values, as well as, differences observed with temperature. Results indicated that hemoglobin is stable over a wide temperature range.

TABLE 4

Hgb (g/dL)

| | Fresh Normal Bloods | | | Fresh Normal Bloods | | |
|---|---|---|---|---|---|---|
| | 60° F. | 75° F. | 75° F.–60° F. | 85° F. | 75° F. | 75° F.–85° F. |
| n = | 34 | 34 | 34 | 24 | 24 | 24 |
| Mean | 13.85 | 13.77 | −0.09 | 13.75 | 13.7 | −0.05 |
| SD | 1.32 | 1.36 | | 1.04 | 1.03 | |
| | Fresh Abnormal Bloods | | | Fresh Abnormal Bloods | | |
| | 60° F. | 75° F. | 75° F.–60° F. | 85° F. | 75° F. | 75° F.–85° F. |
| n = | 18 | 18 | 18 | 16 | 16 | 16 |
| Mean | 9.71 | 9.53 | −0.18 | 11.08 | 10.96 | −0.12 |
| SD | 3.74 | 3.74 | | 4.47 | 4.35 | |

EXAMPLE 5

A multipurpose diluent was prepared using the components and preferred ranges listed in Table 1. A commercial hematology control, a commercial hematology calibrator and three fresh bloods from normal donors were tested on a COULTER STKS. The instrument was placed in an environmental chamber at a controlled temperature of 60° F. and a portion of the samples were tested. Thereafter, the temperature was raised to 90° F. and another portion of the samples were tested. In addition, for each test conducted at extreme temperatures, a comparator instrument was run at 75° F., using another portion of the samples. Table 5 presents mean values for recovered hemoglobin values, as well as, differences observed with temperature. Results indicated that hemoglobin measurement is stable over a wide temperature range.

TABLE 5

HEMOGLOBIN DIFFERENCES WITH TEMPERATURE VARIATION FROM 60° F. TO 90° F. DILUENT OF THE INVENTION

|  | 60° F. | 75° F. | 75–60° F. | 90° F. | 75° F. | 75–90° F. |
| --- | --- | --- | --- | --- | --- | --- |
| Blood Cell Control | 17.13 | 16.98 | −0.15 | 17 | 16.98 | −0.02 |
| Blood Sample #1 | 5.71 | 5.57 | −0.14 | 5.53 | 5.57 | 0.04 |
| Blood Sample #2 | 10.96 | 10.83 | −0.13 | 10.75 | 10.83 | 0.08 |
| Blood Sample #3 | 21.11 | 20.97 | −0.14 | 20.91 | 20.97 | 0.06 |

The invention has been described with reference to particularly preferred embodiments. It will be appreciated, however, that various changes can be made without departing from the spirit of the invention, and such changes are intended to fall within the scope of the appended claims.

What is claimed is:

1. A multipurpose blood diluent not containing hexahydro-1,3,5 tris(2-hydroxethyl)-s-triazine useful in analysis of red blood cells, white blood cells, platelets and hemoglobin concentration in a blood sample, said diluent comprising:
   a) a first compound selected from the group consisting of ethylenediamine tetraacetic acid, ethylenediamine tetraacetic acid derivatives and combinations thereof wherein said first compound is in a concentration of from 2.5 to 11 grams per liter;
   b) a second compound selected from the group consisting of imidazole, imidazole derivatives and combinations thereof;
   c) an alkaline metal chloride; and
   d) a third compound selected from the group consisting of alkaline metal sulfate and alkaline metal salt of organic acids, said alkaline metal salt of organic acids selected from the group consisting of tartrate, formate, lactate, acetate, citrate and pyruvate and combinations thereof, wherein the first compound and second compound are in an amount effective to provide reproducible hemoglobin and cell volume measurements over a temperature range from 55° F. to 105° F. and wherein said diluent is an electrolyte capable of conducting electrical current, isotonic so that it stabilizes blood cell volume and has a neutral pH.

2. The diluent of claim 1, wherein said imidazole derivatives are selected from the group consisting of phenylimidazole, methylimidazole, ethylimidazole and butylimidazole.

3. The diluent of claim 1, which further comprises a cell stabilizing agent.

4. The diluent of claim 1, wherein said diluent further comprises a preservative composition in a concentration of less than 0.5% by weight.

5. The diluent of claim 4, wherein said diluent further comprises a cell stabilizing agent in an amount effective to prevent platelet aggregation.

6. The diluent of claim 5, wherein said cell stabilizing agent is 4-aminobenzoic acid esters and derivatives thereof.

7. The diluent of claim 4, wherein said preservative composition is selected from the group consisting of n-(hydroxymethyl)-N-(1,3-dihydroxymethyl-2,5-dioxo4-imidazolidinyl)-N'-(hydroxymethyl)urea; 5-chloro-2-methyl4-isothiazolin-3-one and 2-methyl4-isothiazolin-3-one; and combinations thereof.

8. The diluent of claim 1, wherein said diluent has an osmolality from 250 to 380 mOsm.

9. The diluent of claim 1, wherein said diluent has a pH from 6.5 to 7.6.

10. A method for analyzing a blood sample containing blood cells comprising:
   a) mixing a blood sample containing blood cells with a multipurpose blood diluent to form a diluted blood sample, said diluent comprising i) a first compound selected from the group consisting of ethylenediamine tetraacetic acid, ethylenediamine tetraacetic acid derivatives and combinations thereof, wherein said first compound is in a concentration of from 2.5 to 11 grams per liter; ii) a second compound selected from the group consisting of imidazole, imidazole derivatives and combinations thereof; iii) an alkaline metal chloride; and iv) a third compound selected from the group consisting of alkaline metal sulfate and alkaline metal salt of organic acids, said alkaline metal salt of organic acids selected from the group consisting of tartrate, formate, lactate, acetate, citrate and pyruvate and combinations thereof; wherein said diluent does not contain hexahydro-1,3,5 tris(2-hydroxethyl)-s-triazine; and wherein the first compound and second compound are in an amount effective to provide reproducible hemoglobin and cell volume measurements over a temperature range from 55° F. to 105° F. and wherein said diluent is an electrolyte capable of conducting electrical current, isotonic so that it stabilizes blood cell volume and has a neutral pH; and
   b) analyzing said diluted blood sample to determine a physical parameter of said blood cells.

11. The method of claim 10, wherein said blood cells comprise red blood cells.

12. The method of claim 11 wherein said analyzing said diluted blood sample to determine at least one physical parameter comprises analyzing to determine mean cell volume of said red blood cells.

13. The method of claim 10, which further comprises mixing a lytic reagent with said diluted blood sample to lyse red blood cells prior to said analyzing said diluted blood sample.

14. The method of claim 13, wherein said blood cells comprise white blood cells.

15. The method of claim 14, wherein said analyzing of said diluted blood sample to determine at least one physical parameter of said blood cells comprises an automated differential analysis of white blood cells to determine at least three subpopulations of white blood cells.

16. The method of claim 15, wherein said analyzing of said diluted blood sample to determine at least one physical parameter of said blood cells comprises an automated differential analysis of the white blood cells to determine at least five subpopulations of white blood cells.

17. The method of claim 15, wherein said lytic reagent comprises an aqueous solution of at least one quaternary ammonium salt.

18. The method of claim 13, wherein said analyzing said diluted blood sample to determine at least one physical parameter of said blood cells comprises analyzing to determine the number of platelets.

19. The method of claim 13, wherein said analyzing said diluted blood sample to determine at least one physical parameter of said blood cells comprises analyzing to determine hemoglobin content.

* * * * *

UNITED STATES PATENT AND TRADEMARK OFFICE
CERTIFICATE OF CORRECTION

PATENT NO. : 5,935,857
DATED : August 10, 1999
INVENTOR(S) : Mirta I. Riesgo, et al It is certified that error appears in the above-identified patent and that said Letters Patent is hereby corrected as shown below:

Column 11, line 7, change "13" to --11--

Signed and Sealed this

Eighteenth Day of July, 2000

Attest:

Q. TODD DICKINSON

*Attesting Officer*     *Director of Patents and Trademarks*